(12) United States Patent
Bolling et al.

(10) Patent No.: US 12,318,296 B2
(45) Date of Patent: Jun. 3, 2025

(54) MITRAL LEAFLET TETHERING

(71) Applicant: Pipeline Medical Technologies, Inc., Santa Rosa, CA (US)

(72) Inventors: Steven F. Bolling, Ann Arbor, MI (US); Randall T. Lashinski, Windsor, CA (US)

(73) Assignee: Pipeline Medical Technologies, Inc., Newark, DE (US)

( * ) Notice: Subject to any disclaimer, the term of this patent is extended or adjusted under 35 U.S.C. 154(b) by 0 days.

(21) Appl. No.: 18/335,589

(22) Filed: Jun. 15, 2023

(65) Prior Publication Data

US 2023/0397992 A1 Dec. 14, 2023

Related U.S. Application Data

(63) Continuation of application No. 16/024,439, filed on Jun. 29, 2018, now abandoned, which is a (Continued)

(51) Int. Cl.
*A61F 2/24* (2006.01)
*A61B 17/04* (2006.01)
(Continued)

(52) U.S. Cl.
CPC ........ *A61F 2/2466* (2013.01); *A61B 17/0401* (2013.01); *A61B 17/0469* (2013.01); (Continued)

(58) Field of Classification Search
CPC .................. A61F 2/2466; A61F 2/2457; A61F 2220/0008; A61F 2220/0016; (Continued)

(56) References Cited

U.S. PATENT DOCUMENTS 4,677,065 A 6/1987 Buchbjerg et al.
4,969,870 A 11/1990 Kramer et al.
(Continued)

FOREIGN PATENT DOCUMENTS

CN 101495049 7/2009
CN 101553190 10/2009
(Continued)

OTHER PUBLICATIONS

Carpentier, M.D., Alain, "Cardiac Valve Surgery—the 'French Correction'", The Journal of Thoracic and Cardiovascular Surgery, Sep. 1983, vol. 86, No. 3, pp. 323-337.
(Continued)

*Primary Examiner* — Jing Rui Ou
(74) *Attorney, Agent, or Firm* — Faegre Drinker Biddle & Reath LLP

(57) ABSTRACT

This disclosure includes apparatuses and techniques to access the right ventricle via trans-femoral vein threading a catheter or catheters to the apex or bottom of the right ventricle. Piercing through the venous or right side of the heart in the interventricular septal wall to access the left ventricle a catheter can be passed to turn upward pointing to the mitral valve. From this access point in the left ventricle the flail mitral leaflet can be sutured and tethered pulling it back into position and reattached with a grounding anchor in the right ventricle or imbedding the anchor into the septal wall. The interventricular septal wall crossing technique could include the passing of a coaxial catheter through the first access catheter where the first access catheter could act as a guide to direct the internal or second coaxial catheter toward the flail mitral leaflet.

10 Claims, 14 Drawing Sheets

Related U.S. Application Data continuation of application No. PCT/US2016/069567, filed on Dec. 30, 2016.

(60) Provisional application No. 62/383,338, filed on Sep. 2, 2016, provisional application No. 62/273,300, filed on Dec. 30, 2015.

(51) Int. Cl.
*A61M 25/00* (2006.01)
*A61M 25/01* (2006.01)
A61B 17/00 (2006.01)

(52) U.S. Cl.
CPC ....... *A61F 2/2457* (2013.01); *A61M 25/0054* (2013.01); *A61M 25/0147* (2013.01); A61B 2017/00292 (2013.01); A61B 2017/00876 (2013.01); A61B 2017/0409 (2013.01); A61B 2017/0419 (2013.01); A61B 2017/0427 (2013.01); A61B 2017/0441 (2013.01); A61B 2017/048 (2013.01); A61F 2220/0008 (2013.01); A61F 2220/0016 (2013.01); A61F 2230/0091 (2013.01)

(58) Field of Classification Search
CPC ....... A61F 2230/0091; A61M 25/0054; A61M 25/0147; A61B 17/0401; A61B 17/0469; A61B 2017/00292; A61B 2017/00876; A61B 2017/0409; A61B 2017/0419; A61B 2017/0427; A61B 2017/0441; A61B 2017/048

See application file for complete search history.

(56) References Cited

U.S. PATENT DOCUMENTS

| | | |
|---|---|---|
| 5,329,923 A | 7/1994 | Lundquist |
| 5,456,708 A | 10/1995 | Doan et al. |
| 5,674,217 A | 10/1997 | Wahlstrom et al. |
| 6,269,819 B1 | 8/2001 | Oz |
| 6,458,107 B1 | 10/2002 | Ockuly |
| 6,461,366 B1 | 10/2002 | Seguin |
| 6,569,105 B1 | 5/2003 | Kortenbach et al. |
| 6,626,930 B1 | 9/2003 | Allen et al. |
| 6,629,534 B1 | 10/2003 | St. Goar et al. |
| 6,743,239 B1 | 6/2004 | Kuehn et al. |
| 6,752,813 B2 | 6/2004 | Goldfarb et al. |
| 6,770,083 B2 | 8/2004 | Seguin |
| 6,840,246 B2 | 1/2005 | Downing |
| 6,978,176 B2 | 12/2005 | Lattouf |
| 7,048,754 B2 | 5/2006 | Martin et al. |
| 7,083,628 B2 | 8/2006 | Bachman |
| 7,191,545 B2 | 3/2007 | Yi |
| 7,226,467 B2 | 6/2007 | Lucatero et al. |
| 7,288,097 B2 | 10/2007 | Seguin |
| 7,464,712 B2 | 12/2008 | Oz et al. |
| 7,563,267 B2 | 7/2009 | Goldfarb et al. |
| 7,604,646 B2 | 10/2009 | Goldfarb et al. |
| 7,608,091 B2 | 10/2009 | Goldfarb et al. |
| 7,632,308 B2 | 12/2009 | Loulmet |
| 7,635,386 B1 | 12/2009 | Gammie |
| 7,637,903 B2 | 12/2009 | Lentz et al. |
| 7,655,015 B2 | 2/2010 | Goldfarb et al. |
| 7,666,204 B2 | 2/2010 | Thornton et al. |
| 7,682,369 B2 | 3/2010 | Seguin |
| 7,736,388 B2 | 6/2010 | Goldfarb et al. |
| 7,871,368 B2 | 1/2011 | Zollinger et al. |
| 7,871,433 B2 | 1/2011 | Lattouf |
| 7,887,552 B2 | 2/2011 | Bachman |
| 7,914,515 B2 | 3/2011 | Heideman et al. |
| 7,914,545 B2 | 3/2011 | Ek |
| 8,075,570 B2 | 12/2011 | Bolduc et al. |
| 8,100,923 B2 | 1/2012 | Paraschac et al. |
| 8,172,872 B2 | 5/2012 | Osypka |
| 8,241,304 B2 | 8/2012 | Bachman |
| 8,252,050 B2 | 8/2012 | Maisano et al. |
| 8,273,054 B2 | 9/2012 | St. Germain et al. |
| 8,303,622 B2 | 11/2012 | Alkhatib |
| 8,382,829 B1 | 2/2013 | Call et al. |
| 8,394,113 B2 | 3/2013 | Wei et al. |
| 8,409,273 B2 | 4/2013 | Thornton et al. |
| 8,465,500 B2 | 6/2013 | Speziali |
| 8,475,472 B2 | 7/2013 | Bachman |
| 8,475,525 B2 | 7/2013 | Maisano et al. |
| 8,480,730 B2 | 7/2013 | Maurer et al. |
| 8,535,339 B2 | 9/2013 | Levin et al. |
| 8,545,551 B2 | 10/2013 | Loulmet |
| 8,545,553 B2 | 10/2013 | Zipory et al. |
| 8,603,066 B2 | 12/2013 | Heidman et al. |
| 8,690,939 B2 | 4/2014 | Miller et al. |
| 8,718,794 B2 | 5/2014 | Helland |
| 8,740,940 B2 | 6/2014 | Maahs et al. |
| 8,778,016 B2 | 7/2014 | Janovsky et al. |
| 8,814,824 B2 | 8/2014 | Kauphusman et al. |
| 8,852,213 B2 | 10/2014 | Gammie et al. |
| 8,940,042 B2 | 1/2015 | Miller et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,594 B2 | 2/2015 | Maisano et al. |
| 8,961,596 B2 | 2/2015 | Maisano et al. |
| 9,011,520 B2 | 4/2015 | Miller et al. |
| 9,023,065 B2 | 5/2015 | Bolduc et al. |
| 9,050,187 B2 | 6/2015 | Sugimoto et al. |
| 9,131,939 B1 | 9/2015 | Call et al. |
| 9,180,007 B2 | 11/2015 | Reich et al. |
| 9,198,649 B2 | 12/2015 | Karapetian et al. |
| 9,241,702 B2 | 1/2016 | Maisano et al. |
| 9,259,218 B2 | 2/2016 | Robinson |
| 9,277,994 B2 | 3/2016 | Miller et al. |
| 9,307,980 B2 | 4/2016 | Gilmore et al. |
| 9,314,242 B2 | 4/2016 | Bachman |
| 9,474,606 B2 | 10/2016 | Zipory et al. |
| 9,492,264 B2 | 11/2016 | Fifer et al. |
| 9,572,667 B2 | 2/2017 | Solem |
| 9,579,097 B2 | 2/2017 | Shluzas |
| 9,636,205 B2 | 5/2017 | Lee et al. |
| 9,636,224 B2 | 5/2017 | Zipory et al. |
| 9,668,860 B2 | 6/2017 | Kudlik et al. |
| 9,681,864 B1 | 6/2017 | Gammie et al. |
| 9,681,964 B2 | 6/2017 | MacKenzie |
| 9,693,865 B2 | 7/2017 | Gilmore et al. |
| 9,724,195 B2 | 8/2017 | Goodwin et al. |
| 9,750,493 B2 | 9/2017 | Robinson et al. |
| 9,788,948 B2 | 10/2017 | Gilmore et al. |
| 9,801,720 B2 | 10/2017 | Gilmore et al. |
| 9,814,454 B2 | 11/2017 | Sugimoto et al. |
| 9,877,833 B1 | 1/2018 | Bishop et al. |
| 9,907,547 B2 | 3/2018 | Gilmore et al. |
| 9,907,681 B2 | 3/2018 | Tobis et al. |
| 10,022,114 B2 | 7/2018 | Gilmore et al. |
| 10,039,643 B2 | 8/2018 | Gilmore et al. |
| 10,039,644 B2 | 8/2018 | Navia et al. |
| 10,052,095 B2 | 8/2018 | Gilmore et al. |
| 10,058,323 B2 | 8/2018 | Maisano |
| 10,076,327 B2 | 9/2018 | Ellis et al. |
| 10,076,658 B2 | 9/2018 | Hastings et al. |
| 10,130,791 B2 | 11/2018 | Heideman et al. |
| 10,159,571 B2 | 12/2018 | de Canniere |
| 10,206,673 B2 | 2/2019 | Maisano et al. |
| 10,231,727 B2 | 3/2019 | Sutherland et al. |
| 10,238,491 B2 | 3/2019 | Tobis |
| 10,285,686 B2 | 5/2019 | Gammie et al. |
| 10,376,266 B2 | 8/2019 | Herman et al. |
| 10,543,090 B2 | 1/2020 | Griswold et al. |
| 10,548,733 B2 | 2/2020 | Purcell et al. |
| 10,595,994 B1 | 3/2020 | Christianson et al. |
| 10,617,523 B2 | 4/2020 | Purcell et al. |
| 10,624,743 B2 | 4/2020 | Keidar et al. |
| 10,660,753 B2 | 5/2020 | Pham et al. |
| 10,667,910 B2 | 6/2020 | Bishop et al. |
| 10,675,150 B2 | 6/2020 | Bishop et al. |

(56) References Cited

U.S. PATENT DOCUMENTS

| | | |
|---|---|---|
| 10,682,230 B2 | 6/2020 | Bishop et al. |
| 10,925,731 B2 | 2/2021 | Bishop et al. |
| 11,083,580 B2 | 8/2021 | Purcell et al. |
| 2003/0083674 A1 | 5/2003 | Gibbens |
| 2003/0105519 A1 | 6/2003 | Fasol et al. |
| 2003/0120341 A1 | 6/2003 | Shennib et al. |
| 2003/0130598 A1 | 7/2003 | Manning et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0073216 A1 | 4/2004 | Lieberman |
| 2004/0091600 A1 | 5/2004 | Salome et al. |
| 2004/0097979 A1 | 5/2004 | Svanidze et al. |
| 2004/0162568 A1 | 8/2004 | Saadat et al. |
| 2004/0172046 A1 | 9/2004 | Hlavka et al. |
| 2005/0096694 A1 | 5/2005 | Lee |
| 2005/0119735 A1 | 6/2005 | Spence et al. |
| 2005/0177132 A1 | 8/2005 | Lentz et al. |
| 2005/0177180 A1 | 8/2005 | Kaganov et al. |
| 2005/0251210 A1 | 11/2005 | Westra et al. |
| 2007/0010857 A1 | 1/2007 | Sugimoto et al. |
| 2007/0038230 A1 | 2/2007 | Stone et al. |
| 2007/0038293 A1 | 2/2007 | St. Goar et al. |
| 2007/0118151 A1 | 5/2007 | Davidson |
| 2007/0123979 A1 | 5/2007 | Perier et al. |
| 2007/0219565 A1 | 9/2007 | Saadat |
| 2008/0177281 A1 | 7/2008 | Weitzner et al. |
| 2008/0177304 A1 | 7/2008 | Westra et al. |
| 2008/0195126 A1 | 8/2008 | Solem |
| 2008/0226810 A1 | 9/2008 | Passe et al. |
| 2008/0228165 A1 | 9/2008 | Spence et al. |
| 2008/0228223 A1 | 9/2008 | Alkhatib |
| 2008/0288061 A1 | 11/2008 | Maurer et al. |
| 2008/0294188 A1 | 11/2008 | Appling et al. |
| 2009/0043153 A1 | 2/2009 | Zollinger et al. |
| 2009/0069847 A1 | 3/2009 | Hashiba et al. |
| 2009/0082828 A1 | 3/2009 | Ostroff |
| 2009/0088837 A1 | 4/2009 | Gillinov et al. |
| 2009/0287304 A1 | 11/2009 | Dahlgren et al. |
| 2009/0312773 A1 | 12/2009 | Cabrera |
| 2009/0312790 A1 | 12/2009 | Forsberg et al. |
| 2010/0023118 A1 | 1/2010 | Medlock et al. |
| 2010/0042147 A1* | 2/2010 | Janovsky ............ A61F 2/2457 606/228 |
| 2010/0161041 A1* | 6/2010 | Maisano ............ A61F 2/2487 128/898 |
| 2010/0161042 A1 | 6/2010 | Maisano et al. |
| 2010/0161043 A1 | 6/2010 | Maisano et al. |
| 2010/0249919 A1 | 9/2010 | Gillinov et al. |
| 2010/0280604 A1 | 11/2010 | Zipory et al. |
| 2011/0011917 A1 | 1/2011 | Loulmet |
| 2011/0022083 A1 | 1/2011 | DiMatteo et al. |
| 2011/0040326 A1 | 2/2011 | Wei |
| 2011/0060407 A1 | 3/2011 | Ketai et al. |
| 2011/0106245 A1 | 5/2011 | Miller et al. |
| 2011/0257581 A1 | 10/2011 | Koziczynski et al. |
| 2011/0301698 A1 | 12/2011 | Miller et al. |
| 2012/0065464 A1 | 3/2012 | Ellis et al. |
| 2012/0095505 A1 | 4/2012 | Shluzas |
| 2012/0116418 A1 | 5/2012 | Belson et al. |
| 2012/0116489 A1 | 5/2012 | Khairkhahan et al. |
| 2012/0158021 A1 | 6/2012 | Morrill |
| 2012/0172915 A1 | 7/2012 | Fifer et al. |
| 2013/0035757 A1 | 2/2013 | Zentgraf et al. |
| 2013/0046380 A1 | 2/2013 | Maisano et al. |
| 2013/0096672 A1 | 4/2013 | Reich et al. |
| 2013/0158567 A1 | 6/2013 | Levin et al. |
| 2013/0190741 A1 | 7/2013 | Moll et al. |
| 2013/0197575 A1 | 8/2013 | Karapetian et al. |
| 2013/0197577 A1 | 8/2013 | Wolf et al. |
| 2013/0197578 A1 | 8/2013 | Gregoire et al. |
| 2013/0253639 A1 | 9/2013 | Alkhatib |
| 2014/0031926 A1 | 1/2014 | Kudlik et al. |
| 2014/0142687 A1 | 5/2014 | De Canniere et al. |
| 2014/0142689 A1 | 5/2014 | De Canniere et al. |
| 2014/0243877 A9 | 8/2014 | Lee et al. |
| 2014/0243963 A1 | 8/2014 | Sheps et al. |
| 2014/0350417 A1 | 11/2014 | Van Bladel et al. |
| 2015/0032127 A1 | 1/2015 | Gammie et al. |
| 2015/0119979 A1 | 4/2015 | Maisano et al. |
| 2015/0182255 A1 | 7/2015 | Shivkumar |
| 2015/0230919 A1 | 8/2015 | Chau et al. |
| 2015/0250590 A1 | 9/2015 | Gries et al. |
| 2015/0272586 A1 | 10/2015 | Herman et al. |
| 2015/0313620 A1 | 11/2015 | Suri |
| 2015/0342737 A1 | 12/2015 | Biancucci et al. |
| 2015/0359632 A1 | 12/2015 | Navia et al. |
| 2016/0058557 A1 | 3/2016 | Reich et al. |
| 2016/0143737 A1 | 5/2016 | Zentgraf et al. |
| 2016/0174964 A1 | 6/2016 | Tobis |
| 2016/0192925 A1 | 7/2016 | Bachman |
| 2016/0228117 A1 | 8/2016 | Borden |
| 2016/0240941 A1 | 8/2016 | Stavrianoudakis |
| 2016/0256269 A1 | 9/2016 | Cahalane et al. |
| 2016/0262741 A1 | 9/2016 | Gilmore et al. |
| 2016/0310701 A1 | 10/2016 | Pai |
| 2016/0354082 A1 | 12/2016 | Oz et al. |
| 2016/0367367 A1 | 12/2016 | Maisano et al. |
| 2017/0042658 A1 | 2/2017 | Lee et al. |
| 2017/0043120 A1 | 2/2017 | Heideman et al. |
| 2017/0079797 A1 | 3/2017 | Maisano et al. |
| 2017/0086975 A1 | 3/2017 | Gilmore et al. |
| 2017/0119368 A1 | 5/2017 | Solem |
| 2017/0135817 A1 | 5/2017 | Tylis et al. |
| 2017/0156719 A1 | 6/2017 | Tobis |
| 2017/0156861 A1 | 6/2017 | Longoria et al. |
| 2017/0202657 A1 | 7/2017 | Lee et al. |
| 2017/0202669 A1 | 7/2017 | Schaffner et al. |
| 2017/0252032 A1 | 9/2017 | Hiorth et al. |
| 2017/0258464 A1 | 9/2017 | Gammie et al. |
| 2017/0258588 A1 | 9/2017 | Zipory et al. |
| 2017/0258594 A1 | 9/2017 | Gilmore et al. |
| 2017/0273681 A1 | 9/2017 | Gilmore et al. |
| 2017/0304051 A1 | 10/2017 | Tobis et al. |
| 2017/0340433 A1 | 11/2017 | Berra et al. |
| 2017/0340443 A1 | 11/2017 | Stearns et al. |
| 2018/0064535 A1 | 3/2018 | Gilmore et al. |
| 2018/0185153 A1 | 7/2018 | Bishop et al. |
| 2018/0185179 A1 | 7/2018 | Murphy et al. |
| 2018/0206992 A1 | 7/2018 | Brown |
| 2018/0221148 A1 | 8/2018 | Guidotti et al. |
| 2018/0249993 A1 | 9/2018 | Denti et al. |
| 2018/0289480 A1 | 10/2018 | D'ambra et al. |
| 2018/0303614 A1 | 10/2018 | Schaffner et al. |
| 2018/0311007 A1 | 11/2018 | Tyler, II et al. |
| 2018/0318079 A1 | 11/2018 | Patel et al. |
| 2018/0318083 A1 | 11/2018 | Bolling et al. |
| 2018/0344311 A1 | 12/2018 | Gilmore et al. |
| 2018/0353297 A1 | 12/2018 | Griffin |
| 2018/0360439 A1 | 12/2018 | Niland et al. |
| 2019/0000624 A1 | 1/2019 | Wilson et al. |
| 2019/0015205 A1 | 1/2019 | Rajagopal et al. |
| 2019/0069891 A1 | 3/2019 | Gilmore et al. |
| 2019/0083085 A1 | 3/2019 | Gilmore et al. |
| 2019/0105027 A1 | 4/2019 | Gilmore et al. |
| 2019/0117401 A1 | 4/2019 | Cortez, Jr. et al. |
| 2019/0151090 A1 | 5/2019 | Gross et al. |
| 2019/0175345 A1 | 6/2019 | Schaffner et al. |
| 2019/0175346 A1 | 6/2019 | Schaffner et al. |
| 2019/0183480 A1 | 6/2019 | Hiorth et al. |
| 2019/0183648 A1 | 6/2019 | Trapp et al. |
| 2019/0216599 A1 | 7/2019 | Alkhatib |
| 2019/0216601 A1 | 7/2019 | Purcell et al. |
| 2019/0240023 A1 | 8/2019 | Spence et al. |
| 2019/0314155 A1 | 10/2019 | Franklin et al. |
| 2019/0328530 A1 | 10/2019 | McDaniel et al. |
| 2019/0365539 A1 | 12/2019 | Rabito et al. |
| 2019/0380699 A1 | 12/2019 | Bak-Boychuk et al. |
| 2020/0155798 A1 | 5/2020 | Yang et al. |
| 2020/0297489 A1 | 9/2020 | Bishop et al. |
| 2020/0330228 A1 | 10/2020 | Anderson et al. |
| 2020/0345496 A1 | 11/2020 | Bishop et al. |
| 2020/0390554 A1 | 12/2020 | Pham et al. |
| 2021/0186699 A1 | 6/2021 | Bishop et al. |

(56) References Cited

U.S. PATENT DOCUMENTS

| | | |
|---|---|---|
| 2021/0213259 A1 | 7/2021 | Giasolli et al. |
| 2022/0338990 A1 | 10/2022 | Hammill et al. |
| 2022/0339437 A1 | 10/2022 | Sorajja |

FOREIGN PATENT DOCUMENTS

| | | |
|---|---|---|
| CN | 101184454 | 10/2010 |
| CN | 101902975 | 12/2010 |
| CN | 103491901 | 1/2014 |
| CN | 103635160 | 3/2014 |
| CN | 103813757 | 5/2014 |
| CN | 103889345 | 6/2014 |
| CN | 104000625 | 8/2014 |
| CN | 104582637 | 4/2015 |
| CN | 105555229 | 5/2016 |
| CN | 107569301 | 1/2018 |
| EP | 0476047 A1 | 3/1992 |
| EP | 1400537 A1 | 3/2004 |
| EP | 1 898 802 | 9/2015 |
| EP | 2 979 647 | 2/2016 |
| EP | 3562410 | 11/2019 |
| FR | 2889416 A1 | 2/2007 |
| JP | 2009-500105 A | 1/2009 |
| JP | 2014-523282 | 9/2014 |
| JP | 2019-500998 A | 1/2019 |
| RU | 2219853 | 12/2003 |
| WO | WO 2007/061834 | 5/2007 |
| WO | WO 2007/100268 | 9/2007 |
| WO | WO 2008/005747 | 1/2008 |
| WO | WO 2010/128502 | 11/2010 |
| WO | WO 2012/040865 | 4/2012 |
| WO | 2012/167120 A2 | 12/2012 |
| WO | WO 2013/179295 | 12/2013 |
| WO | WO 2014/134185 | 9/2014 |
| WO | WO 2017/066888 | 4/2017 |
| WO | WO 2017/066889 | 4/2017 |
| WO | WO 2017/066890 | 4/2017 |
| WO | WO 2017/117560 | 7/2017 |
| WO | WO 2018/035378 | 2/2018 |
| WO | WO 2018/126188 | 7/2018 |
| WO | WO 2018/148324 | 8/2018 |
| WO | WO 2018/148364 | 8/2018 |
| WO | WO 2018/160456 | 9/2018 |
| WO | WO 2018/227048 | 12/2018 |
| WO | WO 2019/013994 | 1/2019 |
| WO | WO 2019/074815 | 4/2019 |
| WO | WO 2019/177909 | 9/2019 |
| WO | WO 2019/195860 | 10/2019 |
| WO | WO 2019/231744 | 12/2019 |
| WO | WO 2019/236654 | 12/2019 |
| WO | WO 2020/106705 | 5/2020 |
| WO | WO 2020/109594 | 6/2020 |
| WO | WO 2020/109596 | 6/2020 |
| WO | WO 2020/109599 | 6/2020 |
| WO | WO 2020/123719 | 6/2020 |
| WO | WO 2020/219281 | 10/2020 |
| WO | WO 2020/256853 | 12/2020 |
| WO | WO 2021/257278 | 12/2021 |
| WO | WO 2022/232070 | 11/2022 |

OTHER PUBLICATIONS

Júnior, Francisco Gregori et al., "Surgical Repair of Chordae Tendineae Rupture After Degenerative Valvular Regurgitation Using Standardized Bovine Pericardium", Revista Brasileira de Cirurgia Cardiovascular, Jan. 2013, vol. 28, No. 1, pp. 36-46.

Kobayashi et al., "Ten Year Experience of Chordal Replacement with Expanded Polytetrafluoroethylene in Mitral Valve Repair", Circulation, American Heart Association, Nov. 7, 2000, pp. III-30-34.

Shikata et al., "Repair of Congenitally Absent Chordae in a Tricuspid Valve Leaflet with Hypoplastic Papillary Muscle Using Artificial Chordae", J Card Surg, 25:737-739 (2010).

International Search Report and Written Opinion received in PCT Application No. PCT/US2016/069567, dated Mar. 23, 2017 in 13 pages.

International Preliminary Report on Patentability received in PCT Application No. PCT/US2016/069567, dated Jul. 12, 2018 in 6 pages.

International Search Report and Written Opinion received in PCT Application No. PCT/US2017/069046, dated Jun. 14, 2018 in 10 pages.

International Search Report and Written Opinion received in PCT Application No. PCT/US2019/021480, dated Jul. 15, 2019 in 12 pages.

International Search Report and Written Opinion received in PCT Application No. PCT/US2019/065814, dated Apr. 1, 2020 in 14 pages.

\* cited by examiner

Ruptured Chord

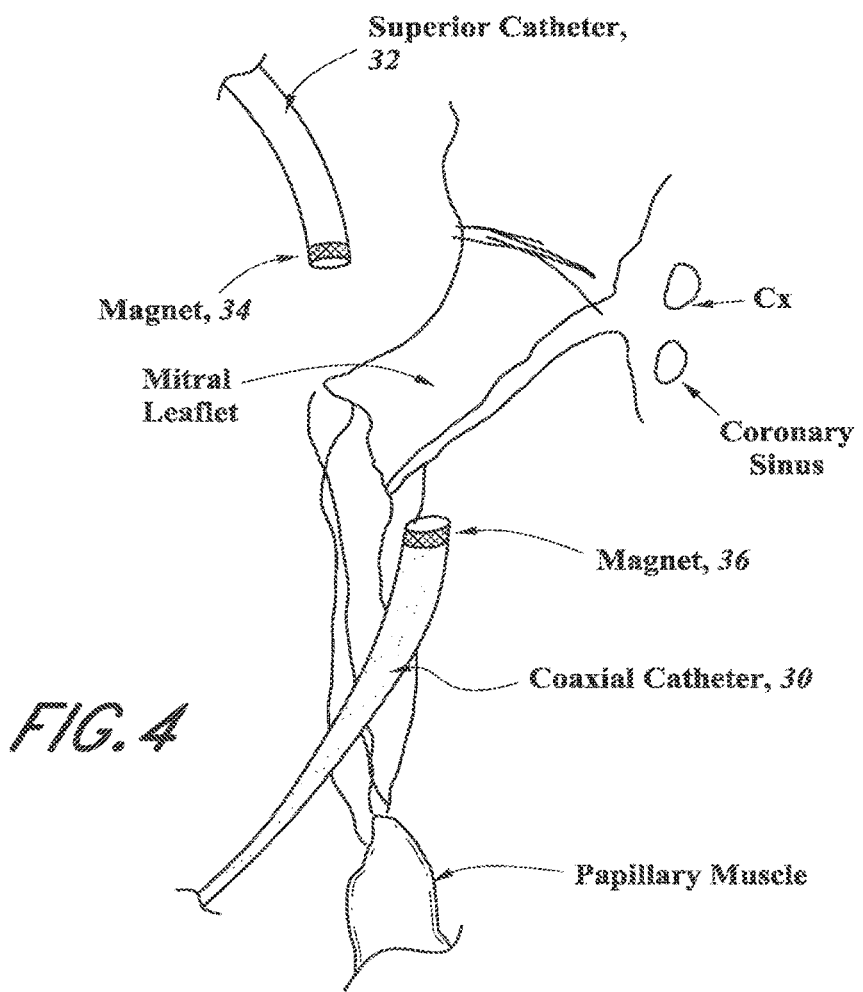

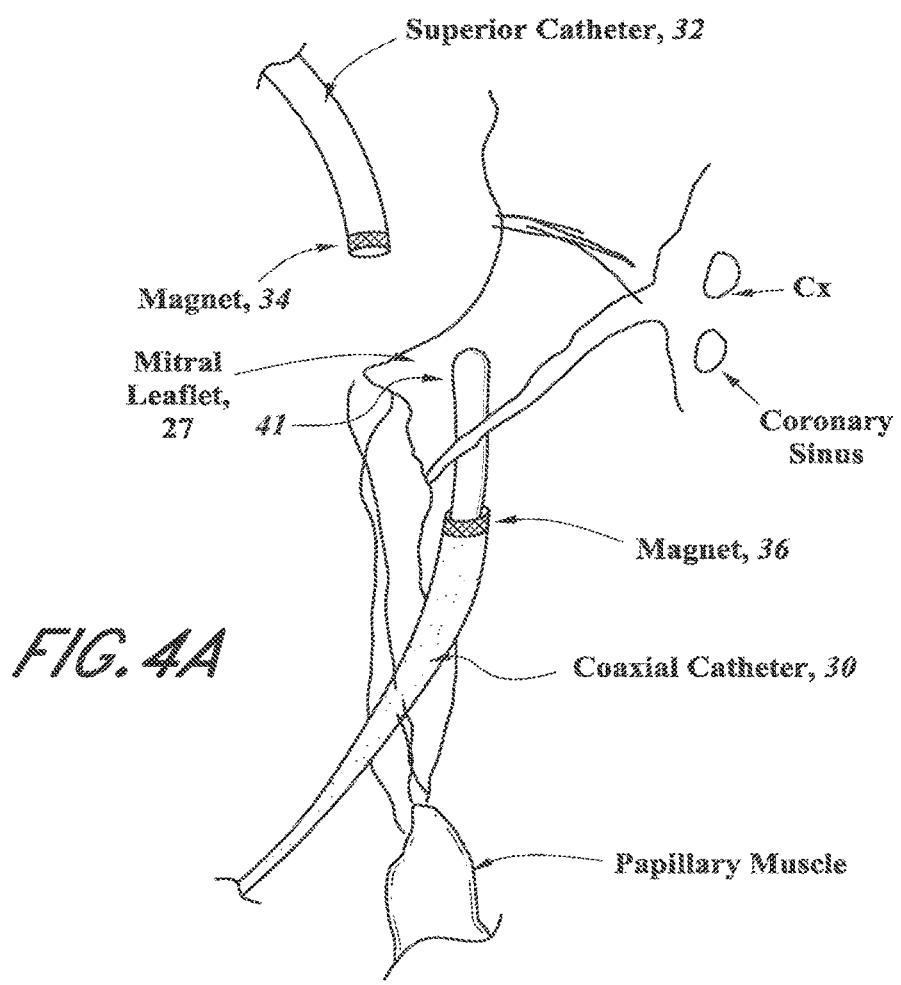

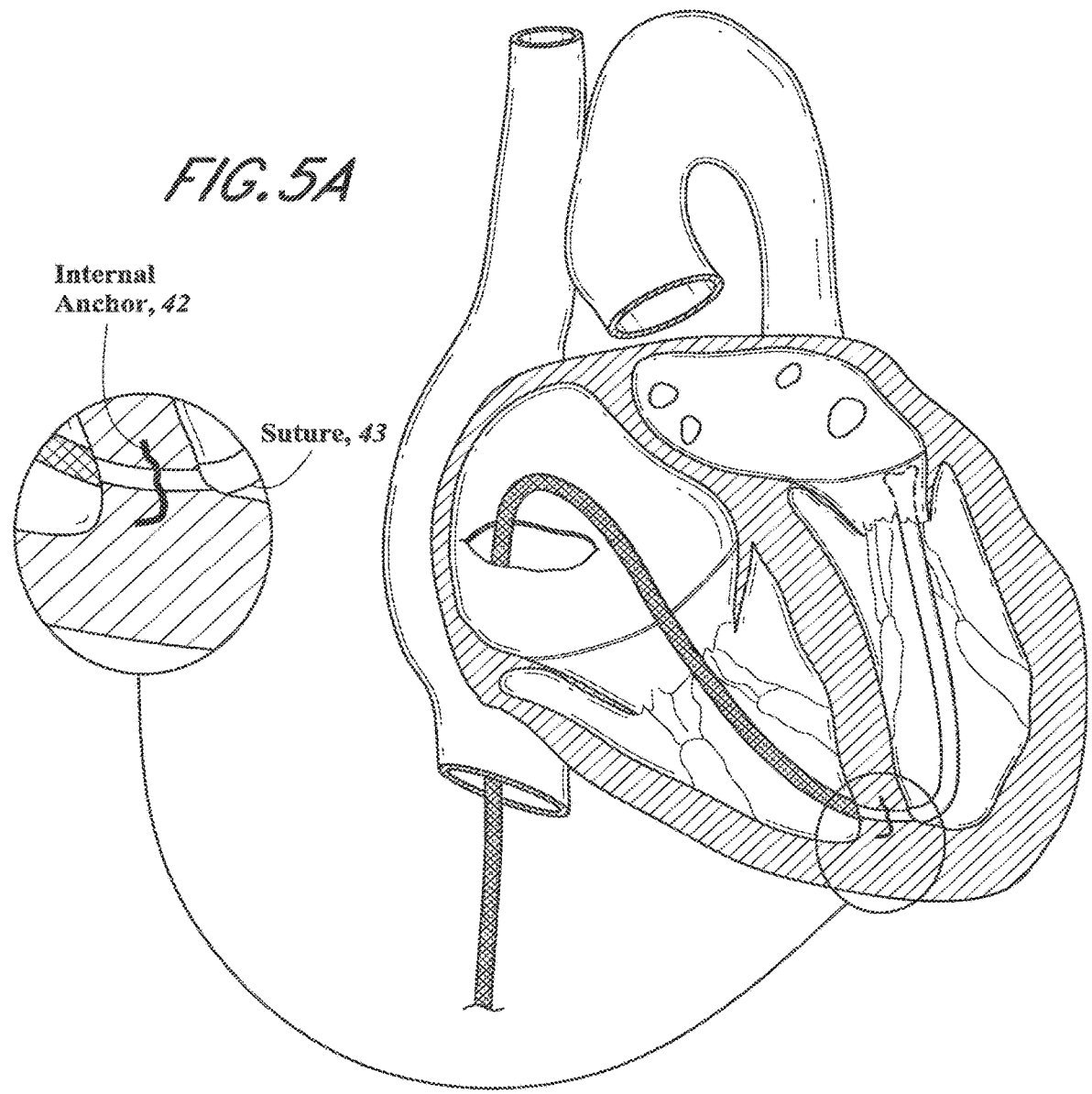

MITRAL LEAFLET TETHERING

INCORPORATION BY REFERENCE TO ANY PRIORITY APPLICATIONS

This application is a continuation of U.S. application Ser. No. 16/024,439, filed Jun. 29, 2018, which is a continuation of PCT Patent Application No. PCT/US2016/069567, filed Dec. 30, 2016, which claims a priority benefit to U.S. Provisional Application No. 62/383,338, filed Sep. 2, 2016 and U.S. Provisional Application No. 62/273,300, filed Dec. 30, 2015, the entire disclosure of each these non-provisional and these provisional applications are hereby incorporated by reference herein for all purposes in their entireties and should be considered a part of this specification.

BACKGROUND

Field

The disclosure relates generally to cardiac treatment devices and techniques, and in particular, to methods and devices for mitral valve repair.

Description of the Related Art

The heart includes four heart valves, which allow blood to pass through the four chambers of the heart in one direction. The four valves are the tricuspid, mitral, pulmonary and aortic valves. The four chambers are the right and left atria (upper chambers) and right and left ventricle (lower chambers).

The mitral valve is formed by two leaflets, which are known as the anterior leaflet and the posterior leaflet, which open and close in response to pressure placed on the leaflets by the pumping of the heart. There are several problems that can develop or occur with respect to the mitral valve. Such problems include mitral valve regurgitation (MR), in which the mitral valve leaflets do not close properly, which can cause leakage of the mitral valve. Severe mitral regurgitation can adversely affect cardiac function and compromise a patient's quality of life and life-span. There are several techniques directed to correcting mitral valve regurgitation, which include valve replacement, chordae tendinea shortening or replacement and mitral annular repair also known as annuloplasty.

Current techniques to correct mitral regurgitation include repairing the mitral valve via open heart surgery while a patient's heart is stopped and the patient is on cardiopulmonary bypass. Such techniques are highly invasive that have inherent risks. It would be desirable to provide a less invasive procedure for repairing a mitral valve.

SUMMARY

One embodiment disclosed herein includes a method of repairing a mitral valve of a patient's heart that comprises accessing a right ventricle of the patient's heart with a catheter extending through a venous or right side of the heart to access the left ventricle and and with the catheter securing a mitral valve leaflet.

Another embodiment disclosed herein is a chordae replacement system that can include a catheter and a chordae replacement implant. The catheter can have an elongate, flexible tubular body with a proximal end and a distal end. The catheter can be configured for transvascular access into the right ventricle, through the intraventricular septum and into the left ventricle. The chordae replacement implant can be deployably carried by the catheter. The chordae replacement implant can comprise an elongate body having a proximal end with a proximal tissue anchor and a distal end with a mitral valve leaflet attachment anchor.

Another embodiment disclosed herein is method of repairing a mitral valve, the method comprising with a catheter transvascularly accessing the right ventricle and extending the catheter through the intraventricular septum and into the left ventricle and deploying a chordae replacement implant with the catheter.

BRIEF DESCRIPTION OF THE DRAWINGS

FIG. 1A illustrates a ruptured chordal attachment.

FIG. 4 illustrates magnets that can be used to position the tips of two catheters relative to one another.

FIG. 4A illustrates passing a suture loop through the mitral leaflet and tethered back through a lower catheter and attached to the anchor at the apex or intraventricular septal wall.

FIG. 5AA illustrates a septal anchor

DETAILED DESCRIPTION OF THE PREFERRED EMBODIMENTS

Figure 1A:
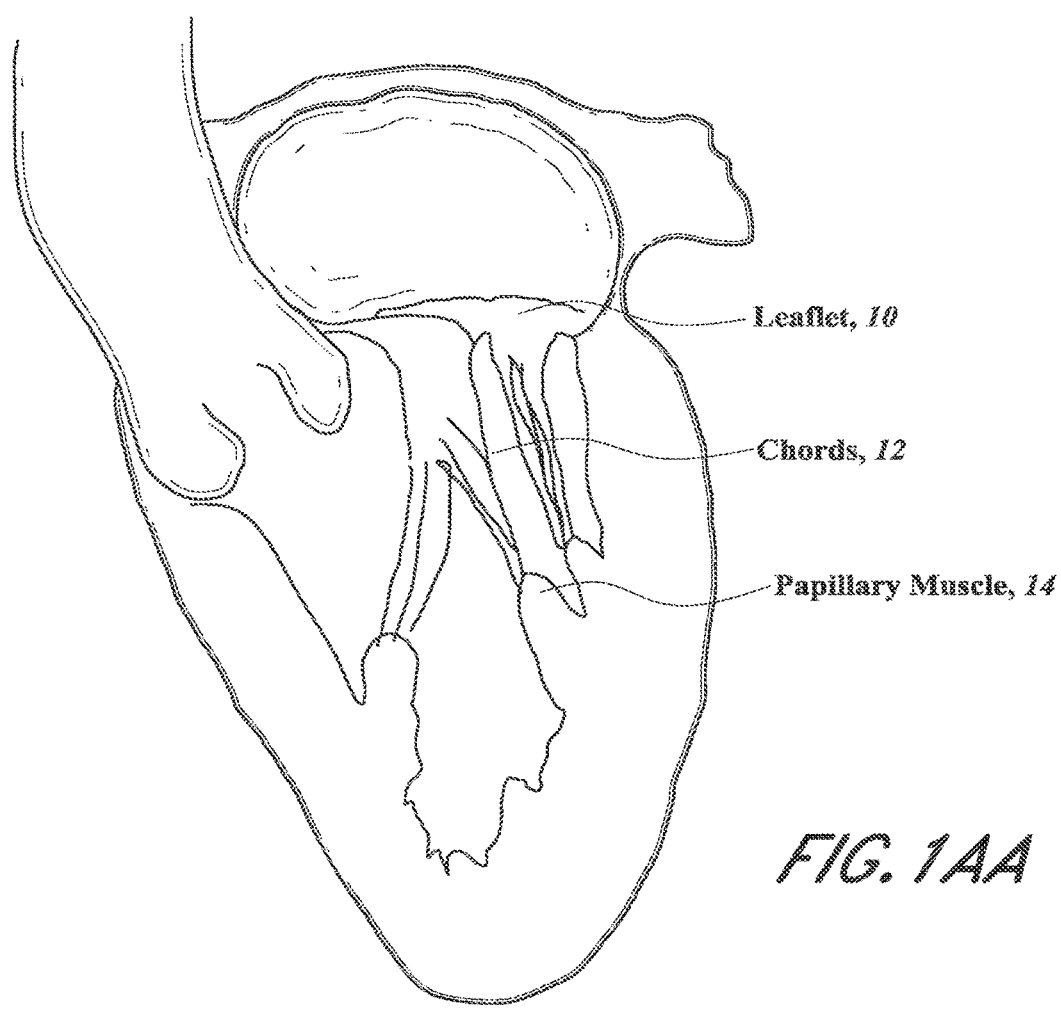
FIG. 1AA illustrates the normal mitral leaflet connections in the left ventricle include chordal attachments from the free margin of the mitral leaflet to the papillary muscles.
Figure 1A:
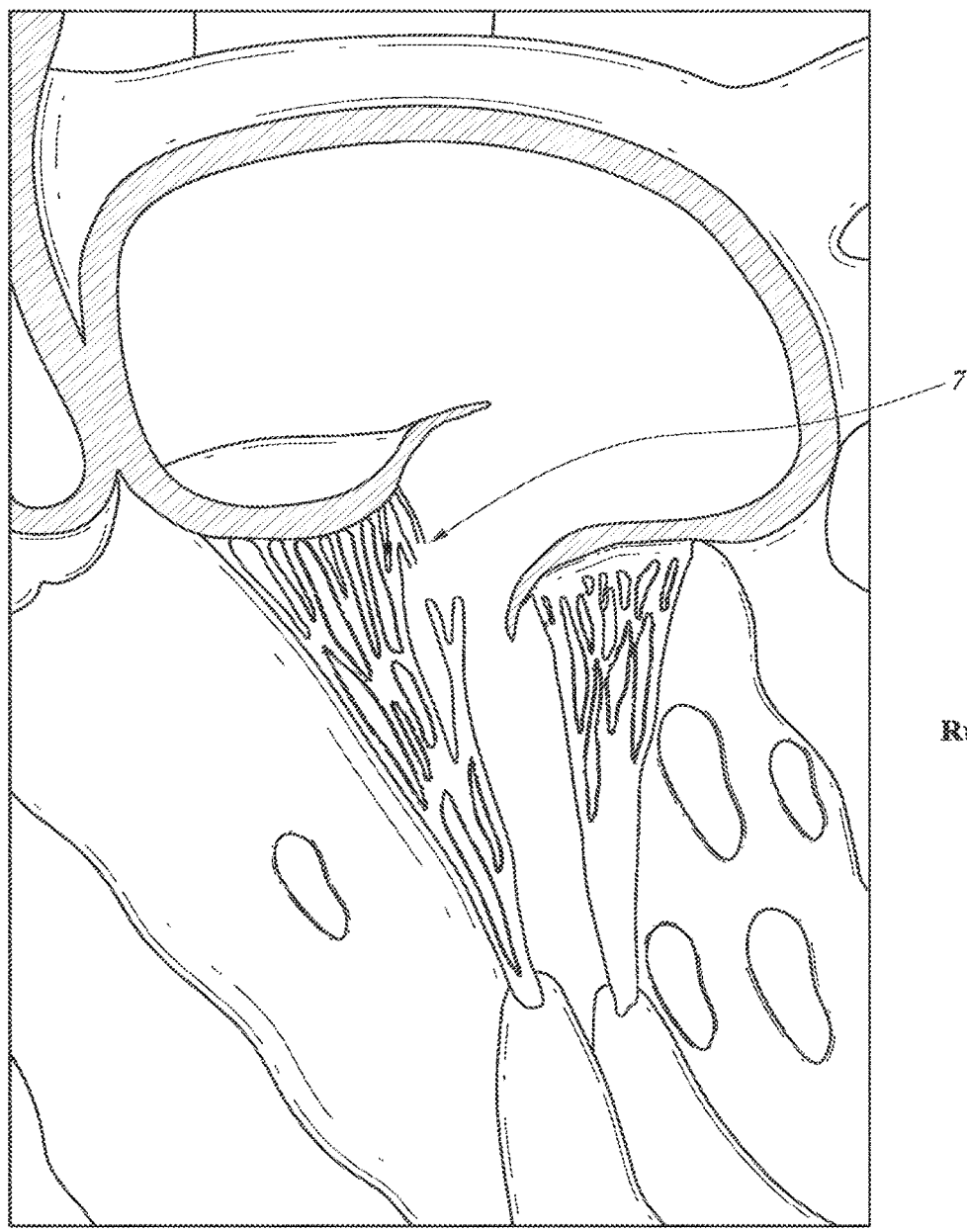

Normal mitral leaflet 10 connections in the left ventricle include chordal attachments 12 from the free margin of the mitral leaflet 10 to the papillary muscles 14, which are shown in FIG. 1AA The repair and reconnection of a flail leaflet (a ruptured chord 7 being shown in FIG. 1A) surgically can be completed with a suture by reattaching the leaflet to a papillary muscle. Another technique would be a trans-apical reconnection of the flail leaflet similar to a technology developed by a company named NeoChord.

Figure 1:
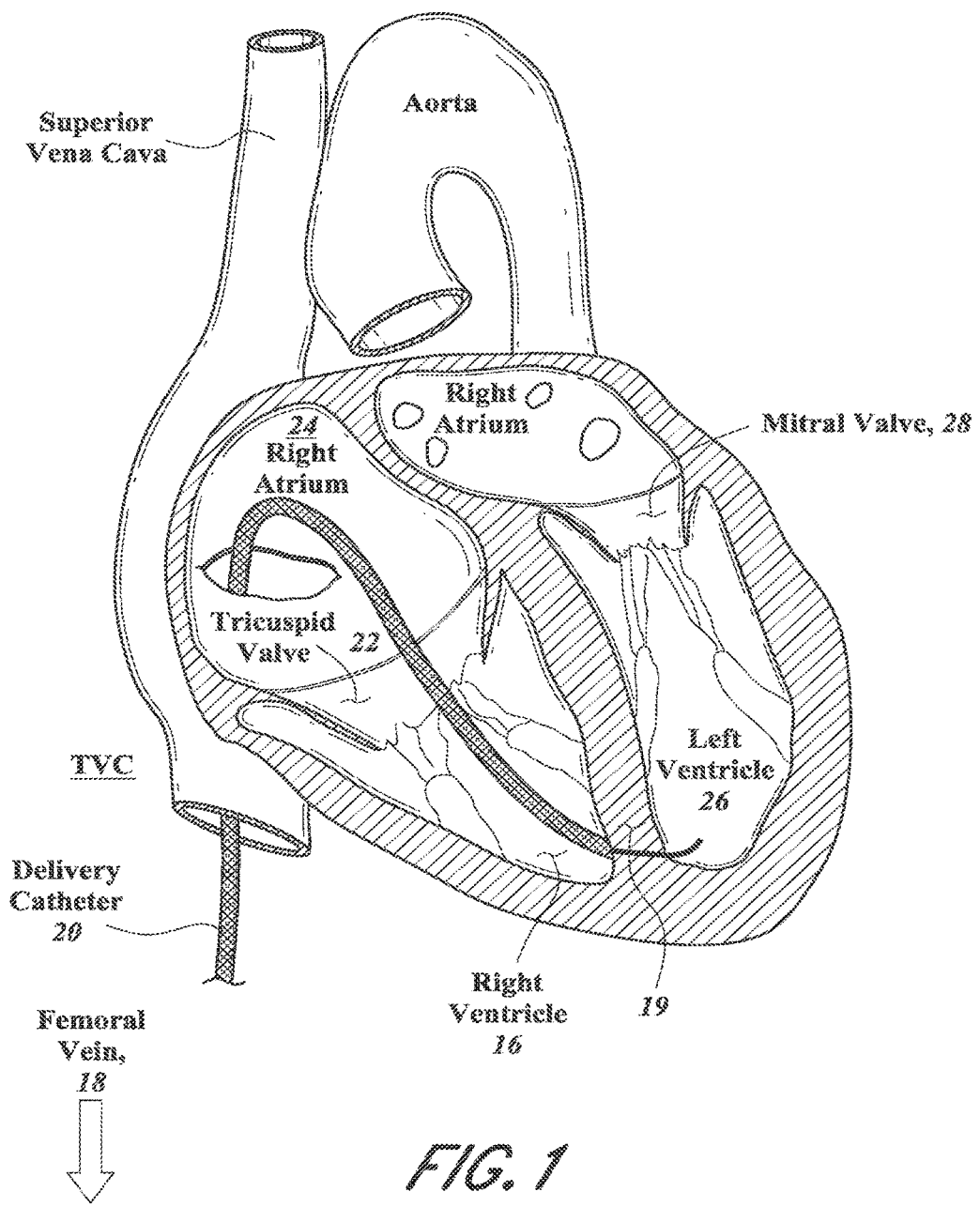
FIG. 1 illustrates a technique to access the right ventricle via trans-femoral vein threading a catheter or catheters to the apex or bottom of the right ventricle.
Figure 2:
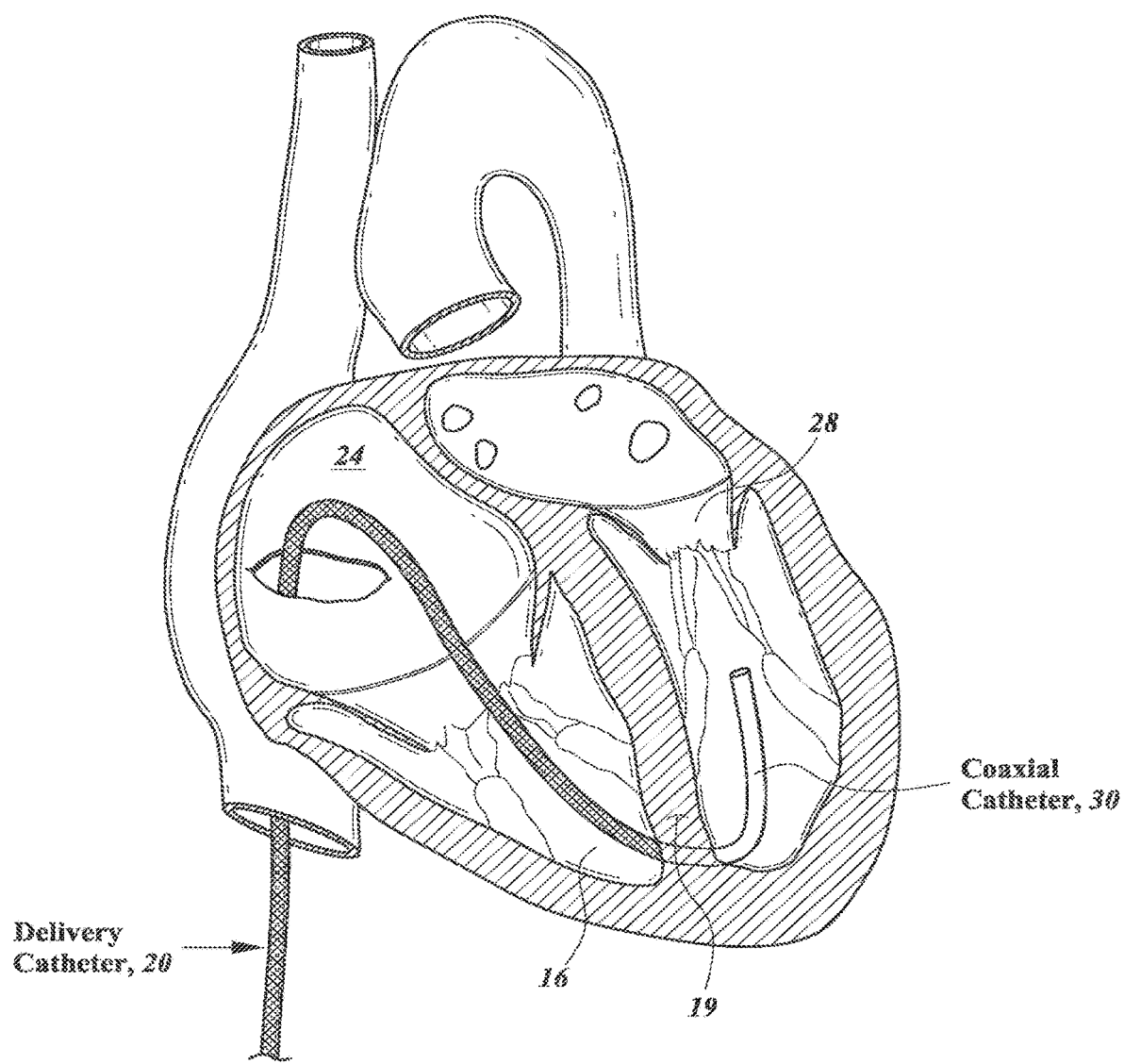
FIG. 2 illustrates a catheter piercing through the venous or right side of the heart in the interventricular septal wall to access the left ventricle.
Figure 3:
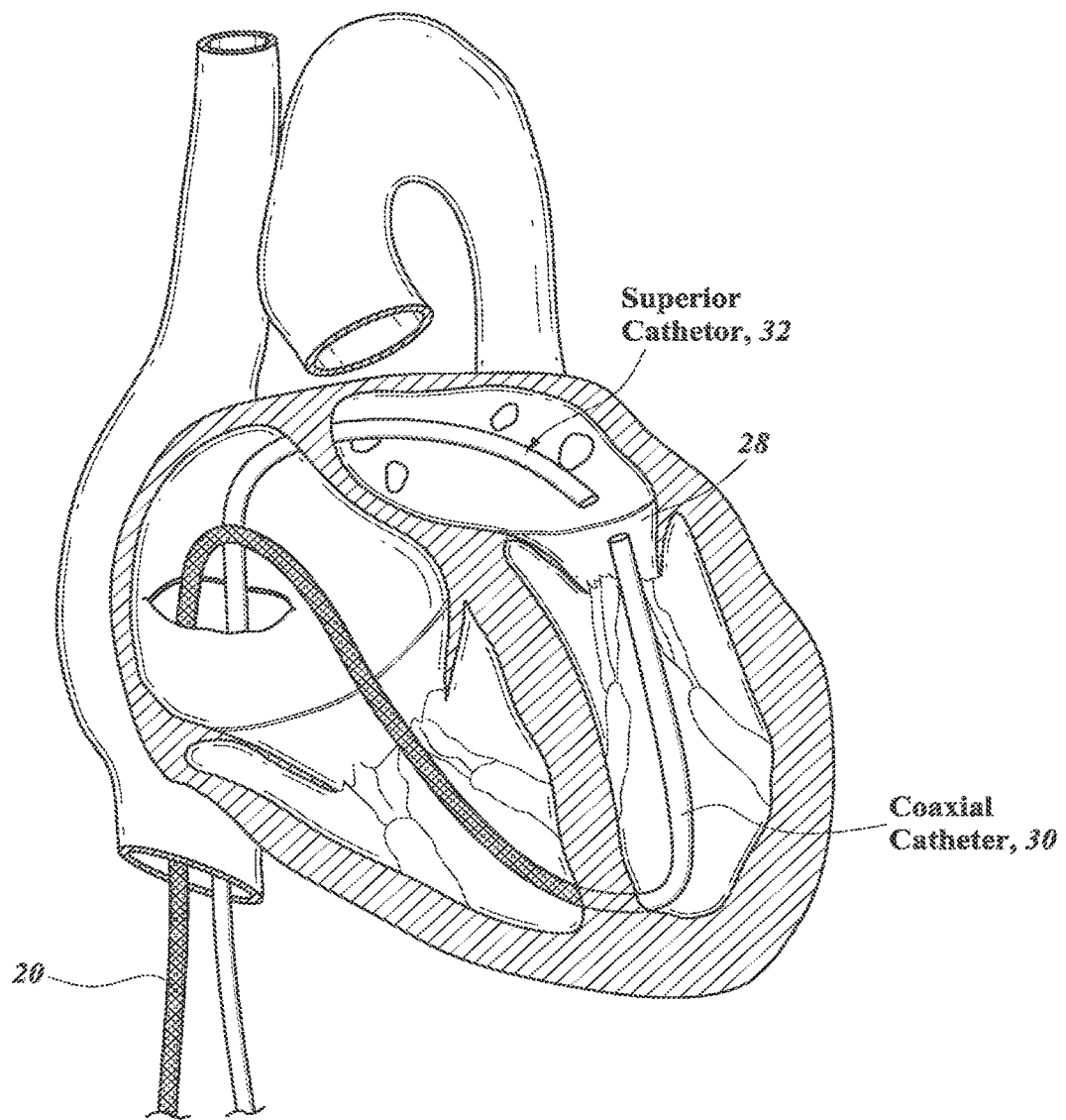
FIG. 3 illustrates first and second catheters that could be steered to position the distal tip to capture the margin of the mitral leaflet.

A different technique would be to access the right ventricle 16 via trans-femoral vein 18 threading a catheter 20 or catheters to the apex or bottom of the right ventricle 16 as shown in FIG. 1. The entry would start in the femoral vein 18 in the groin proceeding up through the inferior vena cava into the right atrium 24 through the tricuspid valve 22 to the bottom of the right ventricle 16. Piercing through the venous or right side of the heart in the interventricular septal wall 19 to access the left ventricle 26 a catheter 20 can be passed to turn upward pointing to the mitral valve 28 as shown in FIG. 2. From this access point in the left ventricle 26 the flail mitral leaflet can be sutured and tethered pulling it back into position and reattached with a grounding anchor in the right ventricle 16 or imbedding the anchor into the septal wall. The interventricular septal wall crossing technique could include the passing of a coaxial catheter 30 through the first access catheter 20 where the first access catheter 20 could act as a guide to direct the internal or second coaxial catheter 30 toward the flail mitral leaflet. Both first and second catheters 20, 30 could be steerable to position the distal tip direction to capture the margin of the mitral leaflet as shown in FIG. 3. A piercing needle could be passed to thread a suture through the mitral leaflet for reattachment or the leaflet to the lower chamber of the heart, into the septal wall or transvers the septal wall and anchor in the right ventricle. Threaded a tether through the mitral leaflet and back through the second internal catheter 30 and attached to the grounding anchor, the leaflet would be pulled into proper position replicating a chordal attachment that may have failed or broken. The attachment of the new suture to the grounding anchor could be achieved through a knot, sliding one-way stopper or other means to join the anchor and suture together. A single line attachment or a plurality of lines would allow the load to be shared or pulled in different force vectors moving the grounding point of the mitral leaflet in different directions. As shown in FIG. 3, a secondary atrial access could be achieved through the venous system superiorly to the mitral valve via trans-septal puncture to pass an additional catheter 32 into the left atrium for positioning above the flail leaflet. Achieving a second securement of the leaflet from above along with below would allow for positive positioning and suture attachment within the leaflet margin as viewed under echo and fluoroscopy. At the tip of each catheter could be a magnet 36, 34 to position the tips of each catheter 30, 32 relative to one another as shown in FIG. 4. The magnet 36, 34 could have a through-hole or central lumen to pass wires, suture 43 or other items longitudinally from one tip to another. A suture loop 41 would be passed through the mitral leaflet 27 and tethered back through the lower catheter 30 and attached to the anchor at the apex or intraventricular septal wall as shown in FIG. 4A.

Figure 5:
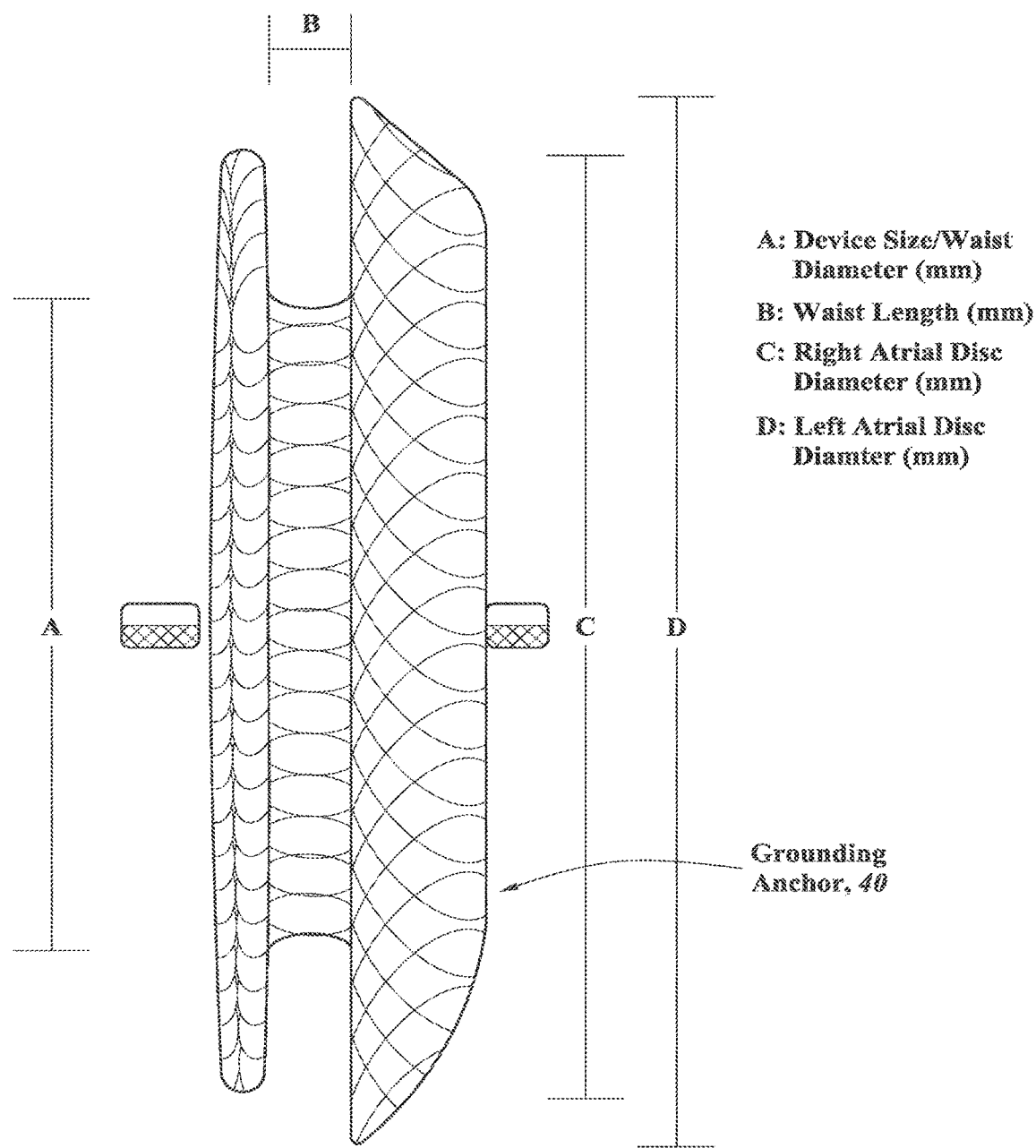
FIG. 5 illustrates a grounding plug.
Figure 5A:
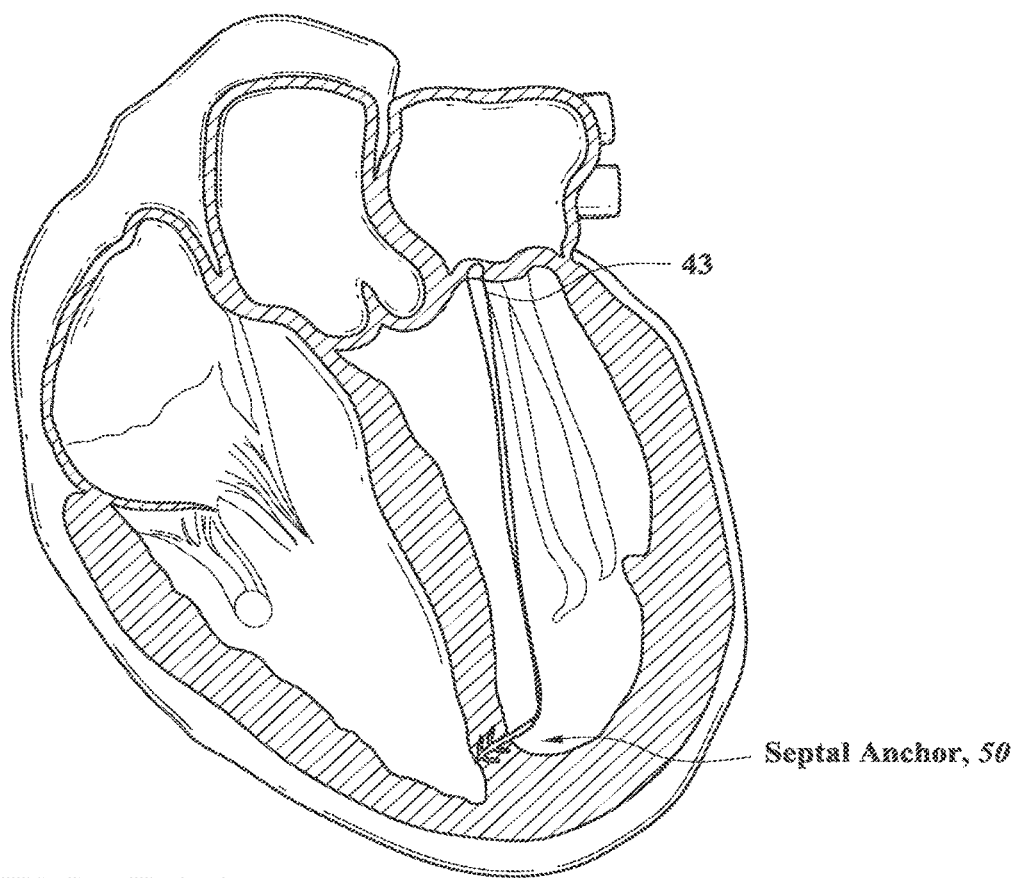
FIG. 5A illustrates an internal anchor within the tissue wall separating the left and right ventricle or interventricular septal wall tissue.
Figure 5B:
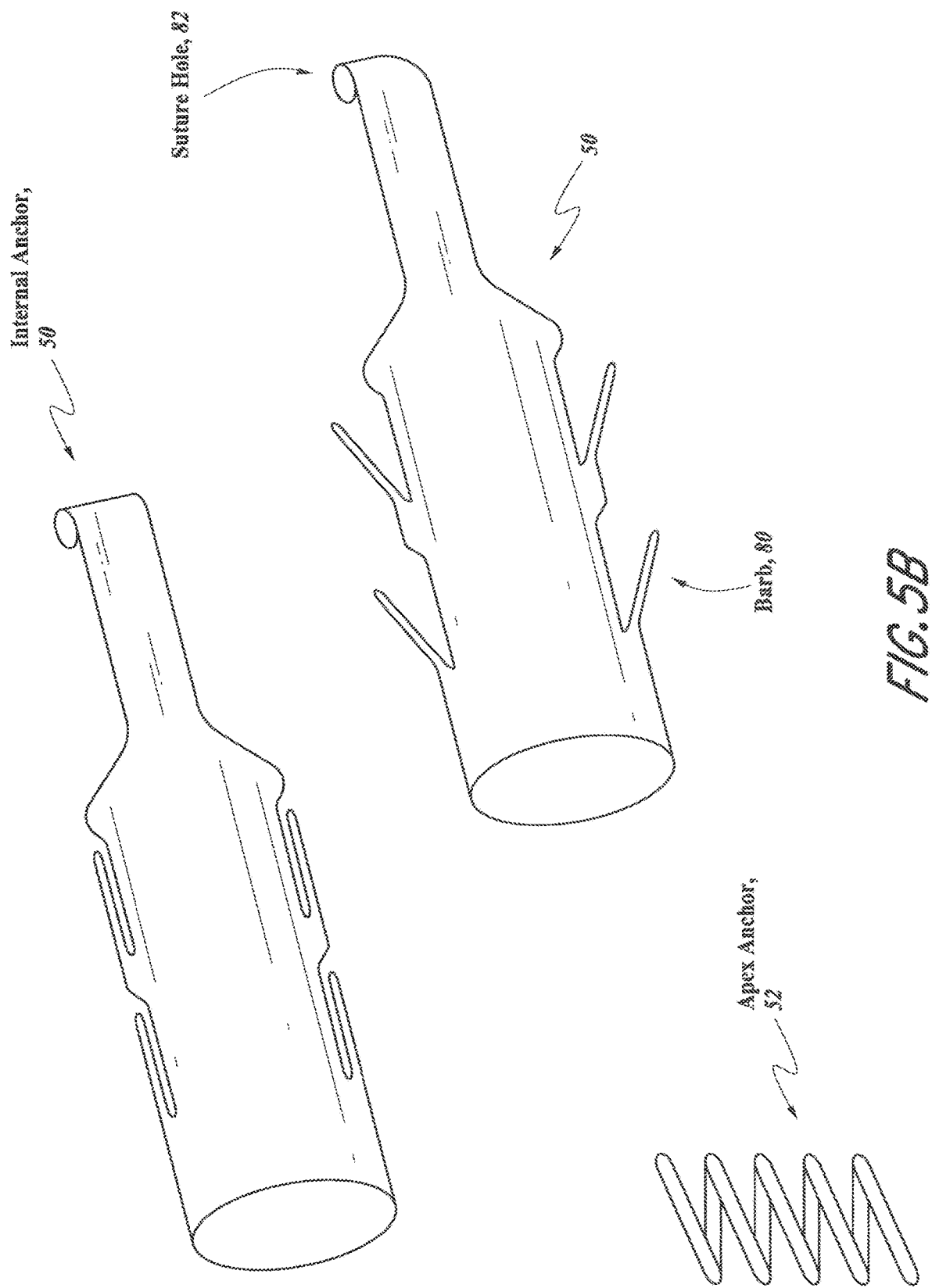
FIG. 5B illustrate embodiments of an internal anchor and apex anchor.
Figure 7:
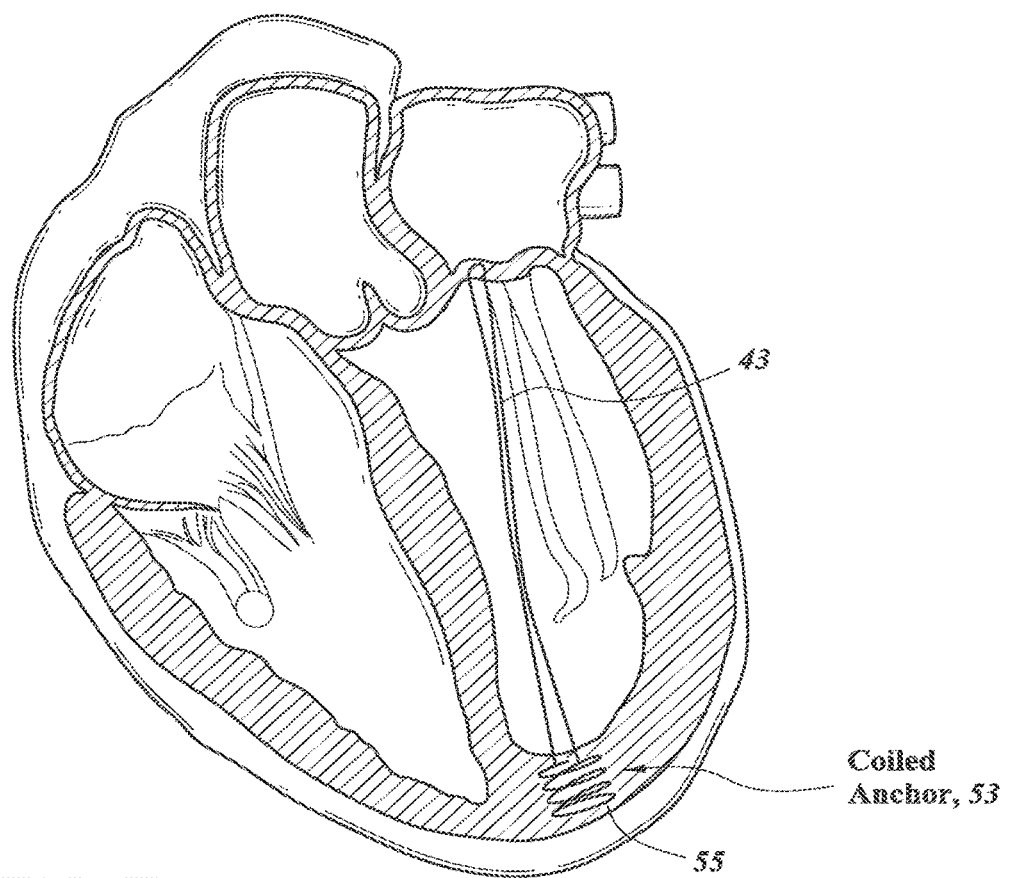
FIG. 7 illustrates a coiled anchor.

The grounding plug or anchor 40 could be similar to an Amplatz device used for closing an ASD or another device to distribute forces to a larger area distributing the load throughout a larger surface area in the right ventricle or within the interventricular septal wall as shown in FIG. 5 Another means to secure the sutures within the right ventricle would be attach them to a pledget 73 or other pad to spread the load within the right ventricle. One alternative technique would be to imbed an internal anchor 42 within the tissue wall separating the left and right ventricle or interventricular septal wall tissue as shown in FIG. 5A. This internal anchors 50 of FIGS. 5B and 5AA could be delivered from above, or from the left atrium, through the septal access and passing through the mitral leaflet to connect the mitral leaflet to the suture 43 and into the septal wall between the right and left ventricle securing it to an internal structure such as an anchor to resist movement during the tensioning of the suture line. As shown in FIG. 5A, the intertal anchor can include barbs 80 and a suture hold 82. It may also be advantageous to extend a section of the anchor into the left atrium away from the septal wall to position the tangent point directly below the attachment point of the mitral leaflet. This would provide a direct line to the attachment points above and below without a torque or moment about the entry to the septal wall and not interfere with any other chordal structures or papillary muscles. A strain relief at the anchor exit may also prohibit fretting of the suture line as its cyclical loading may be an area of stress concentration. Also a coiled anchor 52 (see FIG. 5B) could be delivered from above with a trans-septal access through the mitral valve and into the apex of the heart or into the myocardial tissue as shown in FIG. 7. The coil 55 would allow a contact point connected to the suture line which is farther connected to the mitral leaflet. A plurality of connection points could also be added for additional support or to tether additional ruptured chords. A secondary adjustment could also occur by re-tethering the connection lines by winding, re-knotting or pulling the suture lines post implant procedure.

Figure 8:
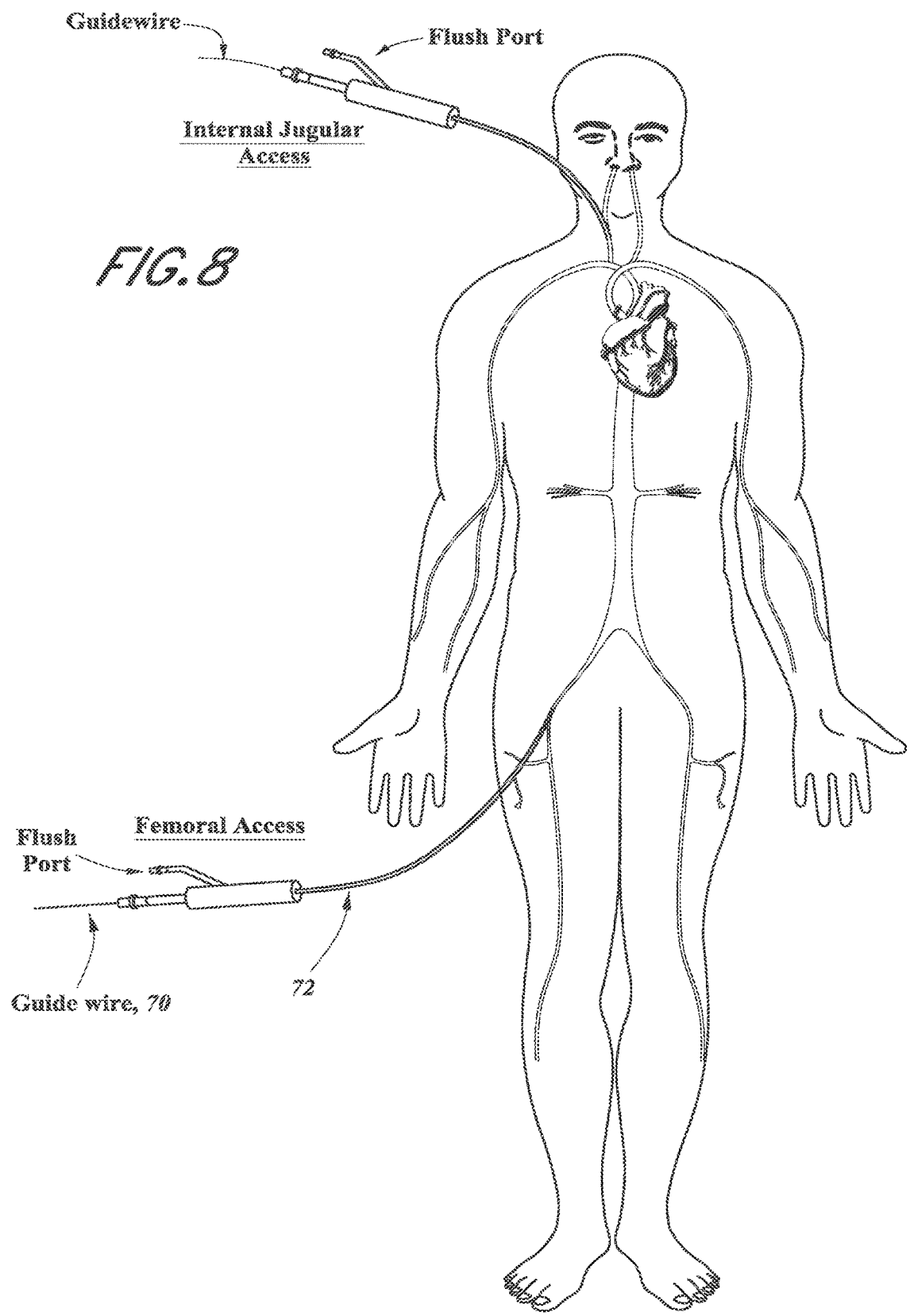
FIG. 8 illustrates access from the jugular vein would also provide access into the vena cava and right ventricle and or access into the left atrium via trans-septal puncture.

Access into the femoral vein could occur with a guidewire 70 measuring about 0.035 inches in diameter and about 180 centimeters in length. An introducer sheath could follow to provide a conduit to pass additional catheters in and out of the femoral access site as shown in FIG. 8. The catheter 72 could measuring about 10 to 24 French in diameter the introducer could be advanced into the femoral vein with a dilator to guide the tip without vessel trauma. The length of the catheter 72 could be about 100 centimeters in length. Advancing the device delivery catheter through this introducer sheath over the guidewire 72 could provide a radiopaque means for tracking the guidewire, introducer sheath and delivery catheter via live x-ray or fluoroscopy. Passed into the inferior vena cava and turning into the right atrium through the tricuspid valve, the catheter can follow the guidewire or be actively shaped or bent through a deflectable catheter at the handle via pull-wire or shaping system. Contrast dye injected into the heart can provide a road map to structural items within the heart. Aiming or steering the catheter and guidewire to the apex of the right ventricle and passing a needle or piercing tool to pass from the right ventricle to the left ventricle will provide access from the femoral vein to the left ventricle accessing the mitral valve.

Figure 6:
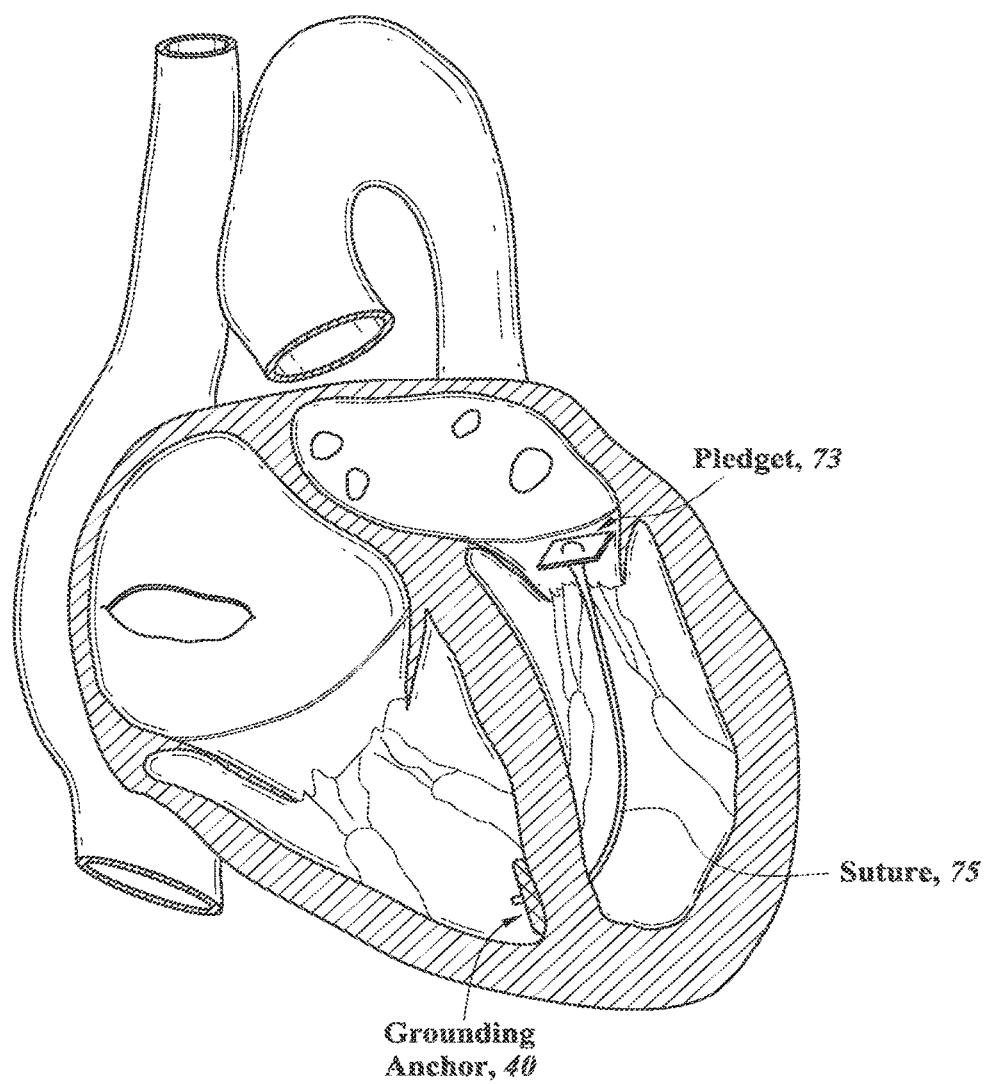
FIG. 6 illustrates a grounding anchor positioned within the heart.

An access pathway to the left atrium through a trans-septaL puncture can be completed by also via the femoral artery at the groin to advance a guidewire and catheter system in a similar manor as described above. This would allow for an above and below intimate contact of the mitral valve leaflets to secure and suture them back into proper positioning. The above-catheter from the left atrium and below—catheter from the left ventricle, via right ventricle, can locate and hold the position of the flail leaflet for suture piercing and tethering back into its proper position to coapt with the adjacent leaflet eliminating the mitral regurgitated blood flow. Piercing needles and strain relieving pledgets 75 could be used to pass suture 75 and distribute the local forces at the leaflet attachment site as shown in FIG. 6. Single or multiple passes through the leaflet will provide a duplication of the normal chorde providing normal leaflet motion. The suture material can be #4 or #5 pTFE, Silk or other common materials used in normal valve repair. The position of the suture would allow for normal left ventricle and mitral valve motion and freedom as the suture would pass in between the papillary muscles and connect to the flail leaflet at one end and into the right ventricle at the other end held by a strain relief in the right ventricle. Access from the jugular vein would also provide access into the vena cava and right ventricle and or access into the left atrium via trans-septal puncture as shown in FIG. 8. This jugular access would eliminate the first 180 degree turn up the femoral vein and into the right ventricle but is not a conventional access for most interventional cardiologist.

Catheters would be constructed of common polymers including nylon, Teflon, urethanes, and other commonly used materials having a proximal and distal end with a guidewire port through s The catheter curves needed would be pre-set, fixed or actively curved through differential forces transmitted via pull wires or tubes to bias one direction or another providing a column compression on one side of the catheter relative to the other. Column and tubular strength could be provided by imbedded coiled wires, braided with ribbon or round wire, laser cut tubes or skeletal structures to form a defined structure and or curve needed to gain access. Variable durometers, construction techniques are well known in the industry to allow for specific pushability, stiffness and curves needed to deliver. Coatings and surface treatments both internally and externally could aid in relative movement between vessel walls and between wires and other catheters. The tensioning means could be provided by a pull-wire extending from the distal end of the catheter to the handle of the proximal section. This pull wire could be activated by rotational screws translated into longitudinal forces pulling a connection to the distal end of the catheter. The overall length of the femoral catheter access would be about 100 cm in length and have a through lumen to accept a guidewire for positioning within the bodies vasculature. The overall length of the internal jugular catheter would be about 60 cm in length. Both catheters would be about 6-20 French in diameter with at least one lumen from the proximal distal end of the delivery system.

Access from the femoral vein will allow for catheterization through the tricuspid valve and into the right ventricle. At the apex of the right ventricle an access will be attained by advancing a needle or catheter in through the septal wall gaining access to the left ventricle. Use of a needle, ultrasonic or coring tool to pass a guidewire from right ventricle to left ventricle is the pathway and access route to repair the mitral valve. Once a needle and or guidewire can be advanced additional tools such as catheters can be utilized to repair the mitral valve. The septal wall can be over 1 centimeter in thickness so maintaining an access port may be achieved by a balloon dilatation, guide catheter or access conduit to pass tools and catheters through during the repair. A steerable sheath, catheter or conduit may allow an easier access direction to the specific area of the mitral valve for repair. Adjustments made rotationally and or angularly can be fixed or locked into position once optimal positioning is obtained. This can be achieved by a pre-shaped curve configuration whereas the catheter is curved down through the tricuspid valve and across the ventricular septal wall then pointing upward toward the mitral valve. This shape can be fixed or variable based upon patient needs and anatomy. Guidewires measuring about 0.035 inches in diameter and about 180 to 300 centimeters in length will allow for catheters to be advanced over and allow exchange of additional tools to be interchanged. Expandable dilators can be used expand areas where tight access is required or larger bore catheters are required. Catheter sizing may start from about 6 French to about 24 French in diameter and range from lengths including 90 centimeters to 160 centimeters. Construction of these catheters can be of normal polymers including nylon, polyurethane, polyethylene or other similar polymers. Braids, coils or laser cut tubes can be used within the catheter construction to better support inner diameters, shapes or curves required. These materials can also include stainless steel, Nitinol, Platinum or MP35N metallic suitable for catheter construction.

Nesting multiple catheters inside one another will provide for additional curves, movement, and translational freedoms. In one embodiment a larger catheter (24 French inner diameter) to access the apex of the right ventricle could be used to position a stable base from which to advance an inner catheter (18 French inner diameter) through the ventricular septal wall and a third catheter could be advanced through this catheter measuring about 14 French inner diameter to advance into the left ventricle directing toward the mitral valve. These catheters would allow for multiple adjustments and angles for various anatomies. The ability to translate, rotate and lock position of each of these catheters together or independently will provide a stable platform to deliver repair tools to the valve. Locking means for each of these catheters nested inside one another can be achieved by an expansion via diameter change using a hydraulic pressure, a mechanical expansion via rotational means creating an eccentric lock or a longitudinal pull to create a differential diameter between the catheters. This push-pull translation could force the catheter to accordion creating a larger bump within one catheter.

Additionally, push pull wires could force the catheters into predetermined shapes and curves in single or multiple plains. By laser cutting a specific pattern into the catheter inner frame a shape can be forced by a pull wire reducing one side of the catheter length while collapsing the round column shape of the catheter creating a shape as determined by the laser cut element internal to the catheter. As an example, a slot could be cut into one side of the tube and a tension wire attached at the distal end of the tube. As tension is applied to the wire, a collapsing of the slotted side of the tube would result in curve or bias to the tubular element. These slots could also be complex shapes to lock the rotational angle into a pre-determined shape. This complex shape could be a chevron, angled cut, radiused shape or another detailed pattern to stop the collapsing of the tube at a predetermined radius. This pattern could also be rotated about the tube to create three-dimensional shapes and curves out of a single plane.

This patterning would be laser cut into the inner tube of the catheter and be constructed from a metallic or polymer and embedded into the wall of the catheter wall.

The first angular curve would be about 180 degrees changing the direction of the catheter from the femoral access through the tricuspid valve and directing toward the apex of the right ventricle. The second curve in this catheter would be about a 90 degree turn toward the ventricular septal wall making a "Shepard's Crook" shape. This 90 degree direction could be also attained with a second inner catheter passed through the first larger diameter catheter to direct the access through the ventricular septal wall. This would require a 90 degree curve to redirect the tip toward the septal wall. Once a penetration of the septal wall is achieved another 90 degree curve would be required to direct the catheter toward the mitral valve. Between these two 90 degree curves and separation of about 1 to 2 centimeters is required to traverse the septal wall tissue. This straight section could be preshaped into the curve configuration and be actuated with a single pull wire or multiple pull wires. The preferred embodiment would utilize the first catheter to attain the 90 degree curve toward the ventricular septal wall.

The next inner catheter directed toward the mitral valve could be advanced toward the valve leaflets in the left ventricle. Directed and placed below the leaflet the catheter tip could locate the free margin of the mitral valve leaflet to secure a tether for a ruptured chord or flail leaflet repair. Single or multiple chords can emanate from a single access point or from separate locations along the valve leaflet. From above through a trans-septal access a second catheter could located the top side of the leaflet along the same free margin of the leaflet. Locating these two catheters coaxially could be achieved through a magnetic tip that is built into the catheter or advanced through each central lumen of the catheters.

Locating these two catheters above and below the leaflet pinching one another with the leaflet sandwiched in between would allow for an access through the leaflet for chordal repair or tethering to secure through the lower access point originating from the right ventricle. The chordal repair could be a PTFE suture or another material suitable for permanent implantation. With the lower access point extending into the right ventricle an anchor could be located completely in the right ventricle or within the ventricular septal wall exposing only the replacement suture material in the left ventricle. Anchor designs can be similar to a barbed anchor with a single or plurality of barbs to engage the tissue, a plug to hold from the right ventricle side of the septal wall or a screw means to engage the tissue in the right or left ventricle. The attachment of the tissue anchor to the chordal leaflet attachment can be adjusted while monitoring the tension of the chord or the echo results live during or after the implantation of the chords and anchor system.

What is claimed is:

1. A method of repairing a mitral valve of a patient's heart, the method comprising:
    advancing a first catheter through a right side of an interventricular septal wall to access a left ventricle and positioning a distal tip of the first catheter below a mitral valve leaflet;
    advancing a second catheter transeptally from a right atrium and into a left atrium and positioning a distal tip of the second catheter above the mitral valve leaflet;
    passing a suture from one of the catheters to another catheter through the mitral valve leaflet; and
    attaching the suture to a ventricular anchor secured to a tissue in the left ventricle, the ventricular anchor coupled to the suture.

2. The method of claim 1, wherein the ventricular anchor is attached to an apex of the left ventricle.

3. The method of claim 1, wherein the ventricular anchor is attached to the interventricular septal wall.

4. The method of claim 1, further comprising passing a piercing tool through the first catheter and through the mitral valve leaflet.

5. The method of claim 1, further comprising holding a position of the mitral valve leaflet with the first catheter and the second catheter.

6. The method of claim 1, further comprising passing the suture through the mitral valve leaflet multiple times.

7. The method of claim 1, further comprising passing multiple sutures through the mitral valve leaflet multiple times.

8. The method of claim 1, wherein the distal tip of the first catheter and the distal tip of the second catheter includes magnets.

9. The method of claim 1, wherein a pledget is attached to the suture to spread a load applied to the mitral valve leaflet.

10. A method of repairing a mitral valve of a patient's heart, the method comprising:
    advancing a first catheter through a septal wall to provide access to a position below a mitral valve leaflet;
    advancing a second catheter to a position above the mitral valve leaflet;
    passing a suture through the mitral valve leaflet such that the suture extends between the first catheter and the second catheter; and
    attaching the suture to a ventricular anchor secured to a tissue in a left ventricle, the ventricular anchor coupled to the suture;
    wherein a distal tip of the first catheter and a distal tip of the second catheter both include magnets.

* * * * *